(12) United States Patent
Kim et al.

(10) Patent No.: US 12,195,431 B2
(45) Date of Patent: Jan. 14, 2025

(54) NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME (71) Applicant: LG Energy Solution, Ltd., Seoul (KR)

(72) Inventors: Hyun Seung Kim, Daejeon (KR); Chul Haeng Lee, Daejeon (KR); Yu Ha An, Daejeon (KR); Jeong Woo Oh, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 860 days.

(21) Appl. No.: 17/421,487

(22) PCT Filed: Jan. 16, 2020

(86) PCT No.: PCT/KR2020/000827
§ 371 (c)(1),
(2) Date: Jul. 8, 2021

(87) PCT Pub. No.: WO2020/149677
PCT Pub. Date: Jul. 23, 2020

(65) Prior Publication Data
US 2022/0089548 A1 Mar. 24, 2022

(30) Foreign Application Priority Data

Jan. 17, 2019 (KR) .................. 10-2019-0006093
Jan. 15, 2020 (KR) .................. 10-2020-0005266

(51) Int. Cl.
*H01M 10/0567* (2010.01)
*C07D 233/84* (2006.01)
(Continued)

(52) U.S. Cl.
CPC ...... *C07D 233/84* (2013.01); *H01M 10/0525* (2013.01); *H01M 10/0567* (2013.01); *H01M 10/4235* (2013.01); *H01M 2300/0025* (2013.01)

(58) Field of Classification Search
CPC ......... H01M 10/0525; H01M 10/0567; H01M 10/4235; H01M 2300/0025; C07D 233/84
See application file for complete search history.

(56) References Cited

U.S. PATENT DOCUMENTS

| 4,526,846 A | 7/1985 | Kearney et al. |
| 4,579,796 A | 4/1986 | Muramatsu |

(Continued)

FOREIGN PATENT DOCUMENTS

| CN | 1692180 A | 11/2005 |
| CN | 101405912 A | 4/2009 |

(Continued)

OTHER PUBLICATIONS

Fijalek Z, Zuman P. Determination of methimazole and Carbimazole using polarography and voltammetry. Analytical letters. Jul. 1, 1990;23(7):1213-33.

(Continued)

*Primary Examiner* — James Lee
(74) *Attorney, Agent, or Firm* — Lerner David LLP (57) ABSTRACT

A non-aqueous electrolyte solution additive, a non-aqueous electrolyte solution for a lithium secondary battery including the same, and a lithium secondary battery including the non-aqueous electrolyte solution are disclosed herein. In some embodiments, the non-aqueous electrolyte solution additive includes a Lewis base compound capable of rapidly reacting with an acid. In some embodiments, the lithium secondary battery including the non-aqueous electrolyte solution has improved high-temperature storage durability.

10 Claims, 5 Drawing Sheets

(51) Int. Cl.
H01M 10/0525 (2010.01)
H01M 10/42 (2006.01)

(56) References Cited

U.S. PATENT DOCUMENTS

| | | |
|---|---|---|
| 8,535,834 B1 | 9/2013 | Yoon |
| 9,728,805 B2 | 8/2017 | Yu et al. |
| 2006/0231484 A1 | 10/2006 | Haring et al. |
| 2007/0224515 A1 | 9/2007 | Xu et al. |
| 2010/0151352 A1 | 6/2010 | Haring et al. |
| 2014/0155566 A1 | 6/2014 | Ignatyen et al. |
| 2014/0272604 A1 | 9/2014 | Lim et al. |
| 2017/0117588 A1 | 4/2017 | Fujita et al. |
| 2017/0256363 A1 | 9/2017 | Matsui et al. |
| 2019/0020063 A1 | 1/2019 | Kim et al. |

FOREIGN PATENT DOCUMENTS

| | | |
|---|---|---|
| CN | 105006594 A | 10/2015 |
| CN | 109686990 A | 4/2019 |
| DE | 3425396 A1 | 2/1985 |
| EP | 3131153 A1 | 2/2017 |
| EP | 3396770 A1 | 10/2018 |
| JP | 2000106211 A | 4/2000 |
| JP | 2003208920 A | 7/2003 |
| JP | 2005116398 A | 4/2005 |
| JP | 2012256505 A | 12/2012 |
| JP | 2018145183 A | 9/2018 |
| KR | 20140050058 A | 4/2014 |
| KR | 20160138402 A | 12/2016 |
| KR | 20180054499 A | 5/2018 |
| WO | 2015102075 A1 | 7/2015 |
| WO | 2016031924 A1 | 3/2016 |

OTHER PUBLICATIONS

International Search Report for PCT/KR2020/000827 mailed May 12, 2020; 2 pages.
Okon UA, Nku CO, Udobang JA, Uwah AF. Comparative Effect of Carbimazole, Glycine Max and Citrus Sinensis on Serum Electrolytes and Urea. RJPBCS. Apr.-Jun. 2013;4(2):395.
Das, D et al. "Antithyroid Drug Carbimazole and Its Analogues: Synthesis and Inhibition of Peroxidase-Catalyzed Iodination of I-Tyrosine", "Journal of Medicinal Chemistry", Oct. 2008, pp. 7313-7317, vol. 51, No. 22, XP055881773.
Extended European Search Report and European Search Opinion for European Patent Application No. 20741907.8 dated Jan. 31, 2022, 10 pages.
Lawson, A. et al., "230. 2-Mercaptoglyoxalines. Part X. The acylation of 2-mercaptoglyoxalines", Journal of the Chemical Society, Jan. 1956 , p. 1103-1108, XP055881775.
Folorunsho, A.A. et al., Serum and Gastric Tissue Electrolyte Levels in Carbimazole-Treated and Levothyroxine-Treaded Male New Zealand White Rabbits, World Journal of Pharmacy and Pharmaceutical Sciences, www.wipps.com, Sep. 2018, pp. 142-155, vol. 7, Issue 10.

NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

The present application is a national phase entry under 35 U.S.C. § 371 of International Application No. PCT/KR2020/000827, filed on Jan. 16, 2020, which claims priority from Korean Patent Application Nos. 10-2019-0006093, filed on Jan. 17, 2019, and 10-2020-0005266, filed on Jan. 15, 2020, the disclosures of which are incorporated by reference herein.

TECHNICAL FIELD

The present invention relates to a non-aqueous electrolyte solution additive, and a non-aqueous electrolyte solution for a lithium secondary battery and a lithium secondary battery which include the same.

BACKGROUND ART

There is a need to develop technology for efficiently storing and utilizing electrical energy as personal IT devices and computer networks are developed with the development of information society and the accompanying dependency of society as a whole on the electrical energy is increased.

Among the technologies developed for this purpose, a technology based on secondary batteries is the most suitable technology for various applications. Since a secondary battery may be miniaturized to be applicable to a personal IT device and may be applied to an electric vehicle and a power storage device, there emerges an interest in the secondary battery. Among these secondary battery technologies, lithium ion batteries, which are battery systems having the theoretically highest energy density, are in the spotlight, and are currently being used in various devices.

Unlike the early days when lithium metal was directly applied to the system, the lithium ion battery system is being realized as a system in which lithium metal is not directly used in the battery, for example, a transition metal oxide material containing lithium is used as a positive electrode material, and a carbon-based material, such as graphite, and an alloy-based material, such as silicon, are used as a negative electrode material in a negative electrode.

The lithium ion battery is largely composed of a positive electrode formed of a transition metal oxide containing lithium, a negative electrode capable of storing lithium, an electrolyte solution that becomes a medium for transferring lithium ions, and a separator, and, among them, a significant amount of research on the electrolyte solution has been conducted while the electrolyte solution is known as a component that greatly affects stability and safety of the lithium ion battery.

In this case, the electrolyte solution for a lithium ion battery is composed of a lithium salt, an organic solvent dissolving the lithium salt, and a functional additive, wherein proper selection of these components is important to improve electrochemical properties of the battery.

As a representative lithium salt currently used, $LiPF_6$, $LiBF_4$, LiFSI (lithium bis(fluorosulfonyl) imide, $LiN(SO_2F)_2$), LiTFSI (lithium bis(trifluoromethanesulfonyl) imide, $LiN(SO_2CF_3)_2$), or LiBOB (lithium bis(oxalate) borate, $LiB(C_2O_4)_2$) is being used, and, with respect to the organic solvent, an ester-based organic solvent or ether-based organic solvent is being used.

With respect to the lithium ion battery, an increase in resistance and a decrease in capacity during charge and discharge or storage at high temperatures have been suggested as a problem that causes performance degradation. Also, among side reactions caused by deterioration of the electrolyte solution at high temperatures, there is a problem of decreasing passivation ability of a film when a by-product, which is generated due to decomposition of the salt at high temperatures, is activated and then decomposes the film formed on surfaces of the positive electrode and the negative electrode, and as a result, this may cause additional decomposition of the electrolyte solution and accompanying self-discharge.

Particularly, with respect to a graphite-based negative electrode mainly used as a negative electrode for a lithium ion battery, since its operating potential is 0.3 V (vs. $Li/Li^+$) or less which is lower than an electrochemical stabilization window of an electrolyte solution used in the lithium ion battery, the electrolyte solution is first reduced and decomposed. The electrolyte solution product thus reduced and decomposed transmits lithium ions, but forms a solid electrolyte interphase (SEI) that suppresses the additional decomposition of the electrolyte solution.

However, as described above, since the passivation ability of the film is degraded due to HF and $PF_5$, which are produced by pyrolysis of $LiPF_6$, a lithium salt widely used in the lithium ion battery while the film is decomposed by decomposition products of the salt at high temperatures or the surface of the electrode deteriorates, dissolution of transition metal occurs from the positive electrode to increase resistance and capacity may be reduced by loss of redox centers. Furthermore, since transition metal ions thus dissolved are electrodeposited on the negative electrode, irreversible capacity is increased by consumption of electrons due to the electrodeposition of the metal and the additional decomposition of the electrolyte, and thus, cell capacity may not only be reduced, but also the resistance may be increased and the graphite negative electrode may be self-discharged.

Therefore, in order to ensure and maintain the passivation ability of the SEI even during high-temperature storage, it is urgent to introduce an electrolyte solution additive which may be reduction-decomposed well, or introduce an additive capable of removing the cause of degradation of a battery at high temperatures by scavenging HF and $PF_5$, the decomposition products of $LiPF_6$ as a typical lithium salt, which are generated due to heat/moisture.

PRIOR ART DOCUMENT

Korean Patent Application Laid-open Publication No. 2014-050058

DISCLOSURE OF THE INVENTION

Technical Problem

An aspect of the present invention provides a non-aqueous electrolyte solution additive using a Lewis base-based compound capable of rapidly reacting with an acid.

Another aspect of the present invention provides a non-aqueous electrolyte solution for a lithium secondary battery which includes the non-aqueous electrolyte solution additive.

Another aspect of the present invention provides a lithium secondary battery including the non-aqueous electrolyte solution for a lithium secondary battery.

Technical Solution

According to an aspect of the present invention, there is provided a non-aqueous electrolyte solution additive which is a compound represented by Formula 1.

[Formula 1]

In Formula 1,
$R_1$ to $R_4$ are each independently hydrogen or a substituted or unsubstituted alkyl group having 1 to 5 carbon atoms.

According to another aspect of the present invention, there is provided a non-aqueous electrolyte solution for a lithium secondary battery which includes a lithium salt, an organic solvent, and the non-aqueous electrolyte solution additive of the present invention as a first additive.

The non-aqueous electrolyte solution for a lithium secondary battery may further include a second additive of at least one selected from the group consisting of vinylene carbonate (VC), 1,3-propane sultone (PS), and ethylene sulfate (Esa).

According to another aspect of the present invention, there is provided a lithium secondary battery including the non-aqueous electrolyte solution for a lithium secondary battery.

Advantageous Effects

According to the present invention, since a compound based on a Lewis base is included as a non-aqueous electrolyte solution additive, a non-aqueous electrolyte solution with properties, which may not only form a stable solid electrolyte interphase (SEI) on a surface of a negative electrode, but may also suppress the dissolution of a positive electrode due to an acid, such as $HF/PF_5$, formed as a decomposition product of a lithium salt, may be provided, and, furthermore, a lithium secondary battery may be prepared in which an increase in resistance during high-temperature storage is improved by including the non-aqueous electrolyte solution.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

Passivation ability of a solid electrolyte interphase (SEI) formed on surfaces of positive/negative electrodes by decomposition of an electrolyte solution is a factor that greatly affects high-temperature storage performance. It is known that acids, such as HF and $PF_5$, which are produced by pyrolysis of $LiPF_6$, a lithium salt widely used in a lithium ion battery, are one of factors that degrade a film. If the surface of the positive electrode is degraded by the attack of these acids, transition metal is dissolved to increase surface resistance of the electrode due to a change in local structure of the surface, and capacity may be reduced because theoretical capacity is reduced by loss of redox centers. Also, since transition metal ions thus dissolved are electrodeposited on the negative electrode reacting in a strong reduction potential range to consume electrons, destruct the film, and expose a new surface, additional electrolyte decomposition is caused to not only increase resistance of the negative electrode, but to also increase irreversible capacity, and thus, there is a limitation in that capacity of a cell is continuously reduced.

Thus, in order to suppress the degradation of the battery, the degradation of the SEI due to $PF_5$ or HF may be prevented by introducing a Lewis base-based additive during the preparation of a non-aqueous electrolyte solution in the present invention, and the transition metal dissolution from the positive electrode may be suppressed by scavenging the acid in the electrolyte solution. In addition, since the Lewis base-based additive is introduced during the preparation of the non-aqueous electrolyte solution in the present invention, an SEI different from a conventional additive may be formed on the surface of the negative electrode while being reduced and decomposed, and thus, high-temperature storage performance of the secondary battery may be further improved by the modification of the SEI.

Non-Aqueous Electrolyte Solution Additive

First, in an embodiment of the present invention, provided is a non-aqueous electrolyte solution additive which is a compound represented by the following Formula 1.

[Formula 1]

In Formula 1, $R_1$ to $R_4$ are each independently hydrogen or a substituted or unsubstituted alkyl group having 1 to 5 carbon atoms.

Specifically, in Formula 1, $R_1$ and $R_4$ may each independently be a substituted or unsubstituted alkyl group having 1 to 5 carbon atoms, and $R_2$ and $R_3$ may each independently be hydrogen or a substituted or unsubstituted alkyl group having 1 to 5 carbon atoms.

More specifically, in Formula 1, $R_1$ and $R_4$ may each independently be a substituted or unsubstituted alkyl group having 1 to 4 carbon atoms, and $R_2$ and $R_3$ may each independently be hydrogen or a substituted or unsubstituted alkyl group having 1 to 3 carbon atoms.

For example, in Formula 1, $R_1$ and $R_4$ may be a substituted or unsubstituted alkyl group having 1 to 3 carbon atoms, and $R_2$ and $R_3$ may be hydrogen.

Since the compound represented by Formula 1 contains a —N—(C=S)—N— functional group acting as a Lewis base in its structure, the compound represented by Formula 1 may scavenge a Lewis acid, such as HF and $PF_5$, decomposition products generated by the decomposition of anions of the lithium salt, in the electrolyte solution. Thus, the compound represented by Formula 1 may prevent additional decomposition of the electrolyte solution of the battery due to destruction of the film by suppressing a degradation behavior due to a chemical reaction of the film on the surface of the positive electrode or negative electrode which is caused by the Lewis acid. Therefore, self-discharge of the battery and the degradation behavior of the battery during high-temperature storage may be finally prevented.

Also, since a C=S functional group and a —N—CO—O— functional group, which are included in the structure of the compound represented by Formula 1, are easily reduced on the surface of the negative electrode, a stable SEI with high passivation ability may be formed on the surface of the negative electrode. Thus, high-temperature durability of the negative electrode itself may not only be improved, but amounts of the transition metals electrodeposited on the negative electrode itself may also be reduced, and furthermore, a self-discharge reaction of the graphite-based or silicon-based negative electrode due to an additional reduction decomposition reaction of the electrolyte solution, which is generated by instability of the SEI, may be prevented.

Through the comprehensive effect, since the non-aqueous electrolyte solution additive, as the compound represented by Formula 1 of the present invention, may stably form an SEI and may prevent the destruction of the film on the positive/negative electrodes due to the decomposition of the lithium salt, it may suppress the self-discharge reaction of the battery, and, accordingly, it may improve initial discharge capacity characteristics of the lithium ion battery and characteristics such as suppression of resistance during high-temperature storage.

The compound represented by Formula 1 may include a compound represented by Formula 1a below.

[Formula 1a]

Non-Aqueous Electrolyte Solution for Lithium Secondary Battery

According to another embodiment, the present invention provides a non-aqueous electrolyte solution for a lithium secondary battery which includes a lithium salt, an organic solvent, and the non-aqueous electrolyte solution additive of the present invention as a first additive.

Hereinafter, each component of the non-aqueous electrolyte solution of the present invention will be described in more detail.

(1) Lithium Salt

Any lithium salt typically used in an electrolyte solution for a lithium secondary battery may be used as the lithium salt without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $ClO_4^-$, $BF_4^-$, $B_{10}Cl_{10}^-$, $PF_6^-$, $CF_3SO_3^-$, $CH_3CO_2^-$, $CF_3CO_2^-$, $AsF_6^-$, $SbF_6^-$, $AlCl_4^-$, $AlO_4^-$, $CH_3SO_3^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $SCN^-$, and $(CF_3CF_2SO_2)_2N^-$ as an anion.

Specifically, the lithium salt may include at least one selected from the group consisting of LiCl, LiBr, LiI, $LiClO_4$, $LiBF_4$, $LiB_{10}Cl_{10}$, $LiPF_6$, $LiCF_3SO_3$, $LiCH_3CO_2$, $LiCF_3CO_2$, $LiAsF_6$, $LiSbF_6$, $LiAlCl_4$, $LiAlO_4$, $LiCH_3SO_3$, LiFSI (lithium bis(fluorosulfonyl) imide, $LiN(SO_2F)_2$), LiTFSI (lithium bis(trifluoromethanesulfonyl) imide, $LiN(SO_2CF_3)_2$), and LiBETI (lithium bisperfluoroethanesulfonimide, $LiN(SO_2C_2F_5)_2$). More specifically, the lithium salt may include a single material selected from the group consisting of $LiPF_6$, $LiBF_4$, $LiCH_3CO_2$, $LiCF_3CO_2$, $LiCH_3SO_3$, LiFSI, LiTFSI, and $LiN(C_2F_5SO_2)_2$, or a mixture of two or more thereof.

The lithium salt may be appropriately changed in a normally usable range but may specifically be included in a concentration of 0.1 M to 3 M, for example, 0.8 M to 2.5 M in the electrolyte solution. If the concentration of the lithium salt is greater than 3 M, there are disadvantageous in that a lithium ion-transfer effect is reduced due to an increase in viscosity of the non-aqueous electrolyte solution and the formation of a uniform SEI is difficult due to a decrease in wettability of the non-aqueous electrolyte solution.

(2) Organic Solvent

A type of the organic solvent is not limited as long as the organic solvent may minimize decomposition due to an oxidation reaction during charge and discharge of the battery and may exhibit desired characteristics with the additive. For example, a carbonate-based organic solvent, an ether-based organic solvent, or an ester-based organic solvent may be used alone or in mixture of two or more thereof.

The carbonate-based organic solvent among the organic solvents may include at least one of a cyclic carbonate-based organic solvent and a linear carbonate-based organic solvent. Specifically, the cyclic carbonate-based organic solvent may include at least one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), and may specifically include a mixed solvent of ethylene carbonate with high permittivity and propylene carbonate having a relatively lower melting point than the ethylene carbonate.

Also, the linear carbonate-based organic solvent is an organic solvent having low viscosity and low permittivity, wherein the linear carbonate-based organic solvent may include at least one selected from the group consisting of dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include dimethyl carbonate.

As the ether-based organic solvent, any one selected from the group consisting of dimethyl ether, diethyl ether, dipropyl ether, methylethyl ether, methylpropyl ether, and ethylpropyl ether or a mixture of two or more thereof may be used, but the ether-based solvent is not limited thereto.

The ester-based organic solvent may include at least one selected from the group consisting of a linear ester-based organic solvent and a cyclic ester-based organic solvent In this case, specific examples of the linear ester-based organic solvent may be any one selected from the group consisting of methyl acetate, ethyl acetate, propyl acetate, methyl propionate, ethyl propionate, propyl propionate, and butyl propionate or a mixture of two or more thereof, but the linear ester-based organic solvent is not limited thereto.

Specific examples of the cyclic ester-based organic solvent may be any one selected from the group consisting of γ-butyrolactone, γ-valerolactone, γ-caprolactone, σ-valerolactone, and ε-caprolactone, or a mixture of two or more thereof, but the cyclic ester-based organic solvent is not limited thereto.

The highly viscous cyclic carbonate-based organic solvent well dissociating the lithium salt in the non-aqueous electrolyte solution due to high permittivity may be used as the organic solvent. Also, in order to prepare a non-aqueous electrolyte solution having higher electrical conductivity, the above cyclic carbonate-based organic solvent may be mixed with the low viscosity, low permittivity linear carbonate compound, such as dimethyl carbonate and diethyl carbonate, and the linear ester compound in an appropriate ratio and used as the organic solvent.

Specifically, the cyclic carbonate compound and the linear carbonate compound may be mixed and used as the organic solvent, and a weight ratio of the cyclic carbonate compound:the linear carbonate compound may be in a range of 10:90 to 70:30.

(3) First Additive

The non-aqueous electrolyte solution of the present invention includes the compound represented by Formula 1 as a first additive.

In this case, since descriptions of the non-aqueous electrolyte solution additive overlap with those described above, the descriptions thereof will be omitted.

However, regarding an amount of the non-aqueous electrolyte solution additive, the non-aqueous electrolyte solution additive may be included in an amount of 0.01 wt % to 5 wt %, for example, 0.1 wt % to 3 wt % based on a total weight of the non-aqueous electrolyte solution.

In a case in which the additive is included within the above range, a secondary battery having more improved overall performance may be prepared. In a case in which the amount of the additive is less than 0.01 wt %, a small amount of HF or $PF_5$ may be scavenged, but an effect of continuously scavenge the HF or $PF_5$ may be insignificant, and, in a case in which the amount of the additive is greater than 5 wt %, resistance of the electrode may be increased due to the decomposition of the excessive amount of the additive, or initial capacity due to a side reaction may be reduced.

Thus, in a case in which the amount of the additive is in a range of 0.01 wt % to 5 wt %, for example, 0.1 wt % to 3 wt %, HF and $PF_5$ may be more effectively scavenged while maximally suppressing the increase in the resistance and the reduction in the capacity due to the side reaction.

As described above, since the compound represented by Formula 1, the Lewis base-based compound, is included as the electrolyte solution additive in the present invention, a robust SEI may not only be formed on the surface of the negative electrode, but a by-product that causes the degradation of the battery during high-temperature storage, for example, the Lewis acid, such as HF and $PF_5$, formed by the decomposition of the lithium salt may also be easily scavenged by a functional group containing —N—(C=S)—N—, a Lewis base functional group, and thus, disadvantages, such as the degradation of the SEI or the dissolution of the transition metal from the positive electrode, may be improved.

That is, with respect to the non-aqueous electrolyte solution of the present invention which includes the compound represented by Formula 1 as the additive, since it may scavenge the Lewis acid capable of causing the self-discharge of the battery by attacking the surfaces of the positive electrode and negative electrode in the electrolyte solution, the high-temperature storage performance may be improved by alleviating the self-discharge of the secondary battery.

(4) Second Additive

Furthermore, in order to improve capacity characteristics and cycle characteristics during high-temperature storage and achieve a resistance reduction effect by forming stable films on the surfaces of the negative electrode and positive electrode in addition to the effect induced by the non-aqueous electrolyte solution additive, the non-aqueous electrolyte solution for a lithium secondary battery of the present invention may further include a second additive in addition to the compound represented by Formula 1 as the first additive.

As the second additive which may be additionally included, at least one additive of vinylene carbonate (VC), 1,3-propane sultone (PS), and ethylene sulfate (Esa), which are known to be able to form a more stable SEI on the surface of the negative electrode during an initial activation process, may be used.

The vinylene carbonate (VC), the 1,3-propane sultone (PS), and the ethylene sulfate (Esa) may each be included in an amount of 10 wt % or less, for example, 0.1 wt % to 7 wt % based on the total weight of the non-aqueous electrolyte solution.

If the amount of each of the compounds is greater than 10 wt %, a side reaction in the electrolyte solution may not only excessively occur during charge and discharge of the battery, but the compounds may also not be sufficiently decomposed at high temperatures so that the compounds may be present in the form of an unreacted material or precipitates in the electrolyte solution at room temperature, and accordingly, lifetime or resistance characteristics of the secondary battery may be degraded.

Particularly, a total amount of the second additive included may be in a range of 15 wt % or less, 0.1 wt % to 15 wt %, particularly 0.1 wt % to 10 wt %, preferably 0.5 wt % to 10 wt %, and more preferably 1.0 wt % to 7.0 wt % based on the total weight of the non-aqueous electrolyte solution.

That is, the second additive may be included in an amount of at least 0.1 wt % or more in order to ensure high-temperature durability of the non-aqueous electrolyte solution, and if the amount of the each compound is greater than 10 wt % or the total amount of the second additive is greater than 15 wt %, since the amounts of the organic solvent and lithium salt may be relatively reduced, there is a risk of degrading basic performance of the battery beyond the role of the additive, and thus, it is necessary to appropriately adjust the amount within the above range.

(5) Additive for Forming SEI

Also, the non-aqueous electrolyte solution of the present invention may further include an additional additive which may act as a complementary agent for forming a stable film on the surfaces of the negative electrode and the positive electrode, suppressing the decomposition of the solvent in the non-aqueous electrolyte solution, and improving the mobility of lithium ions.

The additional additive is not particularly limited as long as it is an additive for forming an SEI which may form a stable film on the surfaces of the positive electrode and the negative electrode.

Specifically, as a representative example, the additive for forming an SEI may include at least one additive for forming an SEI which is selected from the group consisting of a halogen-substituted or unsubstituted cyclic carbonate compound, a nitrile compound, a phosphate compound, a borate compound, a lithium salt compound, a sulfate compound, a sultone compound, a fluorinated benzene compound, and a silane compound.

Specifically, the halogen-substituted cyclic carbonate compound may include fluoroethylene carbonate (FEC) and may improve durability of the battery by forming a stable SEI mainly on the surface of the negative electrode during battery activation. The cyclic carbonate compound may include vinyl ethylene carbonate.

The halogen-substituted or unsubstituted cyclic carbonate compound may be included in an amount of 5 wt % or less based on the total weight of the non-aqueous electrolyte solution. In a case in which the amount of the halogen-substituted carbonate compound is greater than 5 wt %, cell swelling inhibition performance and initial resistance may deteriorate.

Also, the nitrile compound may include at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

In a case in which the nitrile compound is used with the above-described electrolyte solution additive, an effect, such as an improvement of high-temperature characteristics, may be expected due to positive electrode/negative electrode film stabilization. That is, the nitrile compound may act as a complementary agent for forming the negative electrode SEI, may play a role in suppressing the decomposition of the solvent in the non-aqueous electrolyte solution, and may play a role in improving the mobility of the lithium ions. The nitrile compound may be included in an amount of 8 wt % or less based on the total weight of the non-aqueous electrolyte solution. In a case in which the total amount of the nitrile compound in the non-aqueous electrolyte solution is greater than 8 wt %, since the resistance is increased due to an increase in the film formed on the surface of the electrode, battery performance may deteriorate.

Furthermore, since the phosphate compound stabilizes $PF_6$ anions in the electrolyte solution and assists in the formation of the positive electrode and negative electrode films, the phosphate compound may improve the durability of the battery. The phosphate compound may include at least one compound selected from the group consisting of lithium difluoro bis(oxalato)phosphate (LiDFOP), lithium difluorophosphate (LiDFP, $LiPO_2F_2$), tis(trimethylsilyl) phosphate (LiTFOP), and tris(2,2,2-trifluoroethyl)phosphate (TFEPa), and the phosphate compound may be included in an amount of 3 wt % or less based on the total weight of the non-aqueous electrolyte solution.

Since the borate compound promotes ion-pair separation of a lithium salt, the borate compound may improve the mobility of lithium ions, may reduce the interfacial resistance of the SEI, and may dissociate a material, such as LiF, which may be formed during the battery reaction but is not well separated, and thus, a problem, such as generation of hydrofluoric acid gas, may be solved. The borate compound may include lithium bis(oxalato)borate (LiBOB, $LiB(C_2O_4)_2$), lithium oxalyldifluoroborate, or tis(trimethylsilyl) borate (TMSB), and the borate compound may be included in an amount of 3 wt % or less based on the total weight of the non-aqueous electrolyte solution.

Also, the lithium salt compound is a compound different from the lithium salt included in the non-aqueous electrolyte solution, wherein the lithium salt compound may include at least one compound selected from the group consisting of LiODFB and $LiBF_4$ and may be included in an amount of 3 wt % or less based on the total weight of the non-aqueous electrolyte solution.

The sulfate compound may include trimethylene sulfate (TMS) or methyl trimethylene sulfate (MTMS), and may be included in an amount of 3 wt % or less based on the total weight of the non-aqueous electrolyte solution.

The sultone compound may include at least one compound selected from the group consisting of 1,4-butane sultone, ethane sultone, 1,3-propene sultone (PRS), 1,4-butene sultone, and 1-methyl-1,3-propene sultone, and may be included in an amount of 0.3 wt % to 5 wt %, for example, 1 wt % to 5 wt % based on the total weight of the non-aqueous electrolyte solution. In a case in which the amount of the sultone compound in the non-aqueous electrolyte solution is greater than 5 wt %, since an excessively thick film is formed on the surface of the electrode, an increase in resistance and a degradation of output may occur and output characteristics may be degraded due to the increase in the resistance caused by the excessive amount of the additive in the non-aqueous electrolyte solution.

The fluorinated benzene compound may include fluorobenzene.

Furthermore, the silane compound may include a compound containing silicon, such as tetravinylsilane, and the compound may be included in an amount of 2 wt % or less based on the total weight of the non-aqueous electrolyte solution.

Two or more additives for forming an SEI may be mixed and used, and the additive for forming an SEI may be included in an amount of 10 wt % or less, and particularly 0.01 wt % to 10 wt %, for example, 0.1 wt % to 5.0 wt % based on the total weight of the electrolyte solution.

In a case in which the amount of the additive for forming an SEI is less than 0.01 wt %, the high-temperature storage characteristics and the gas generation reducing effect to be achieved from the additive may be insignificant, and, in a case in which the amount of the additive for forming an SEI is greater than 10 wt %, the side reaction in the electrolyte solution during charge and discharge of the battery may excessively occur. Particularly, if the excessive amount of the additive for forming an SEI is added, the additive for forming an SEI may not be sufficiently decomposed so that it may be present in the form of an unreacted material or precipitates in the electrolyte solution at room temperature. Accordingly, resistance may be increased to degrade life characteristics of the secondary battery.

Lithium Secondary Battery

Also, in an embodiment of the present invention, there is provided a lithium secondary battery including the non-aqueous electrolyte solution for a lithium secondary battery of the present invention.

Specifically, the lithium secondary battery of the present invention may be prepared by injecting the non-aqueous electrolyte solution of the present invention into an electrode assembly formed by sequentially stacking a positive electrode, a negative electrode, and a separator disposed between the positive electrode and the negative electrode. In this case, those typically used in the preparation of the lithium secondary battery may all be used as the positive electrode, the negative electrode, and the separator which constitute the electrode assembly.

The positive electrode and the negative electrode, which constitute the lithium secondary battery of the present invention, may be prepared by a typical method and used.

(1) Positive Electrode

First, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include a lithium transition metal oxide including lithium and at least one metal selected from cobalt, manganese, nickel, or aluminum, may specifically include lithium-nickel-manganese-cobalt-based oxide with high capacity characteristics and stability of the battery (e.g., $Li(Ni_p\text{-}Co_qMn_{r1})O_2$ (where $0<p<1$, $0<q<1$, $0<r1<1$, and $p+q+r1=1$) or lithium-manganese-based oxide, and may more specifically include lithium-manganese-based oxide.

The lithium-nickel-manganese-cobalt-based oxide may include $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, and $Li(Ni_{0.8}Mn_{0.1}Co_{0.1})O_2$, and the lithium-manganese-based oxide may include $LiMn_2O_4$.

In addition to the lithium-manganese-based oxide, the positive electrode active material of the present invention may further include at least one lithium transition metal oxide selected from the group consisting of lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$ $LiMn_{2-Z1}Co_{Z1}O_4$ (where $0<Z1<2$ etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$)), or lithium-nickel-cobalt-transition metal (M) oxide (e.g., $Li(Ni_{p2}Co_{q2}Mn_{r3}M_{S2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$)).

The positive electrode active material may be included in an amount of 80 wt % to 99 wt % based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene terpolymer, a styrene-butadiene rubber, a fluoro rubber, various copolymers thereof, and the like.

The conductive agent is typically added in an amount of 1 wt % to 30 wt % based on the total weight of the solid content in the positive electrode slurry.

Any conductive agent may be used as the conductive agent without particular limitation so long as it has conductivity without causing adverse chemical changes in the battery, and, for example, a conductive material, such as: graphite; a carbon-based material such as carbon black, acetylene black, Ketjen black, channel black, furnace black, lamp black, or thermal black; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include an organic solvent, such as N-methyl-2-pyrrolidone (NMP), and may be used in an amount such that desirable viscosity is obtained when the positive electrode active material as well as optionally the binder and the conductive agent are included. For example, the solvent may be included in an amount such that a concentration of the solid content in the slurry including the positive electrode active material as well as optionally the binder and the conductive agent is in a range of 50 wt % to 95 wt %, for example, 70 wt % to 90 wt %.

(2) Negative Electrode

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include a single material selected from the group consisting of a lithium-containing titanium composite oxide (LTO); a carbon-based material such as non-graphitizable carbon and graphite-based carbon; a complex metal oxide such as $Li_xFe_2O_3$ (0≤x≤1), $Li_xWO_2$ (0≤x≤1), $Sn_xMe_{1-x}Me'_yO_z$ (Me: manganese (Mn), Fe, lead (Pb), or germanium (Ge); Me': Al, boron (B), phosphorous (P), silicon (Si), Groups I, II and III elements of the Periodic Table, or halogen; 0<x≤1; 1≤y≤3; 1≤z≤8); a lithium metal; a lithium alloy; a silicon-based alloy; a tin-based alloy; a metal oxide such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, and $Bi_2O_5$; and a conductive polymer, such as polyacetylene, or a mixture of two or more thereof.

The negative electrode active material may be included in an amount of 80 wt % to 99 wt % based on a total weight of solid content in the negative electrode active material slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene polymer, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode active material slurry. Any conductive agent may be used as the conductive agent without particular limitation so long as it has conductivity without causing adverse chemical changes in the battery, and, for example, a conductive material, such as: graphite such as natural graphite or artificial graphite; a carbon black such as acetylene black, Ketjen black, channel black, furnace black, lamp black, and thermal black; conductive fibers such as carbon fibers and metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as optionally the binder and the conductive agent are included. For example, the solvent may be included in an amount such that a concentration of the solid content in the negative electrode slurry including the negative electrode active material as well as optionally the binder and the conductive agent is in a range of 50 wt % to 95 wt %, for example, 70 wt % to 90 wt %.

(3) Separator

Also, the separator plays a role in blocking an internal short-circuit between both electrodes and being impregnated with the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

After ethylene carbonate and ethyl methyl carbonate were mixed in a volume ratio of 30:70, a non-aqueous organic solvent was prepared by dissolving $LiPF_6$ and LIFSI in the mixture to have concentrations of 0.7 M and 0.3 M, respectively. A non-aqueous electrolyte solution for a lithium secondary battery was prepared by adding 0.5 g of the compound represented by Formula 1a as a first additive, 1.0 g of ethylene sulfonate and 0.5 g of 1,3-propane sultone as a second additive, 0.1 g of tetravinylsilane, 1.0 g of lithium difluorophosphate, 0.2 g of $LiBF_4$ and 6.0 g of fluorobenzene as an additive for forming an SEI to 90.7 g of the non-aqueous organic solvent.

(Secondary Battery Preparation)

A positive electrode active material ($LiNi_{0.8}Co_{0.1}Mn_{0.1}O_2$:$LiNi_{0.6}Co_{0.2}Mn_{0.2}O_2$=70:30 weight ratio), carbon black as a conductive agent, and polyvinylidene fluoride (PVDF), as a binder, were added to N-methyl-2-pyrrolidone (NMP), as a solvent, at a weight ratio of 97.5:1:1.5 to prepare a positive electrode mixture slurry (solid content: 50 wt %). A 12 μm thick aluminum (Al) thin film, as a positive electrode collector, was coated with the positive electrode mixture slurry, dried, and then roll-pressed to prepare a positive electrode.

A negative electrode active material (SiO:graphite=5:95 weight ratio), SBR-CMC as a binder, and carbon black, as a conductive agent, were added in a weight ratio of 95:3.5:1.5 to water, as a solvent, to prepare a negative electrode mixture slurry (solid content: 60 wt %). A 6 μm thick copper (Cu) thin film, as a negative electrode collector, was coated with the negative electrode mixture slurry, dried, and then roll-pressed to prepare a negative electrode.

The prepared positive electrode, a porous polyolefin-based separator coated with inorganic material particles ($Al_2O_3$), and the negative electrode were sequentially stacked to prepare an electrode assembly.

Subsequently, the assembled electrode assembly was accommodated in a battery case, and the non-aqueous electrolyte solution was injected thereinto to prepare a pouch type lithium secondary battery.

Example 2

(Non-Aqueous Electrolyte Solution Preparation)

After ethylene carbonate and ethyl methyl carbonate were mixed in a volume ratio of 30:70, a non-aqueous organic solvent was prepared by dissolving $LiPF_6$ in the mixture to have a concentration of 1.2 M. A non-aqueous electrolyte solution for a lithium secondary battery was prepared by adding 1.0 g of the compound represented by Formula 1a to 99.0 g of the non-aqueous organic solvent.

(Secondary Battery Preparation)

A pouch type lithium secondary battery was prepared in the same manner as in Example 1 except that the above-prepared non-aqueous electrolyte solution was used instead of the non-aqueous electrolyte solution prepared in Example 1.

Example 3

(Non-Aqueous Electrolyte Solution Preparation)

After ethylene carbonate, ethyl methyl carbonate, and dimethyl carbonate were mixed in a volume ratio of 30:30:40, a non-aqueous organic solvent was prepared by dissolving $LiPF_6$ in the mixture to have a concentration of 1.0 M. A non-aqueous electrolyte solution for a lithium secondary battery was prepared by adding 0.3 g of the compound represented by Formula 1a as a first additive, 3.0 g of VC, 1.0 g of ethylene sulfonate and 0.5 g of 1,3-propane sultone as a second additive to 95.5 g of the non-aqueous organic solvent.

(Secondary Battery Preparation)

A positive electrode active material ($LiNi_{0.7}Co_{0.1}Mn_{0.2}O_2$), carbon black as a conductive agent, and polyvinylidene fluoride (PVDF), as a binder, were added to N-methyl-2-pyrrolidone (NMP), as a solvent, at a weight ratio of 97.5:1:1.5 to prepare a positive electrode mixture slurry (solid content: 50 wt %). A 12 μm thick aluminum (Al) thin film, as a positive electrode collector, was coated with the positive electrode mixture slurry, dried, and then roll-pressed to prepare a positive electrode.

A negative electrode active material (graphite), SBR-CMC as a binder, and carbon black, as a conductive agent, were added in a weight ratio of 95:3.5:1.5 to water, as a solvent, to prepare a negative electrode mixture slurry (solid content: 60 wt %). A 6 μm thick copper (Cu) thin film, as a negative electrode collector, was coated with the negative electrode mixture slurry, dried, and then roll-pressed to prepare a negative electrode.

The prepared positive electrode, a porous polyolefin-based separator coated with inorganic material particles ($Al_2O_3$), and the negative electrode were sequentially stacked to prepare an electrode assembly.

Subsequently, the assembled electrode assembly was accommodated in a battery case, and the non-aqueous electrolyte solution was injected thereinto to prepare a pouch type lithium secondary battery.

Comparative Example 1

(Non-Aqueous Electrolyte Solution Preparation)

After ethylene carbonate and ethyl methyl carbonate were mixed in a volume ratio of 30:70, a non-aqueous organic solvent was prepared by dissolving $LiPF_6$ and LIFSI in the mixture to have concentrations of 0.7 M and 0.3 M, respectively. A non-aqueous electrolyte solution for a lithium secondary battery was prepared by adding 1.0 g of ethylene sulfonate and 0.5 g of 1,3-propane sultone as a second additive, 0.1 g of tetravinylsilane, 1.0 g of lithium difluorophosphate, 0.2 g of $LiBF_4$ and 6.0 g of fluorobenzene as an additive for forming an SEI to 91.2 g of the non-aqueous organic solvent.

(Secondary Battery Preparation)

A pouch type lithium secondary battery was prepared in the same manner as in Example 1 except that the above-prepared non-aqueous electrolyte solution was used instead of the non-aqueous electrolyte solution prepared in Example 1.

Comparative Example 2

(Non-Aqueous Electrolyte Solution Preparation)

After ethylene carbonate, ethyl methyl carbonate, and dimethyl carbonate were mixed in a volume ratio of 30:30:40, a non-aqueous organic solvent was prepared by dissolving $LiPF_6$ in the mixture to have a concentration of 1.0 M. A non-aqueous electrolyte solution for a lithium secondary battery was prepared by adding 3.0 g of VC, 1.0 g of ethylene sulfonate and 0.5 g of 1,3-propane sultone as a second additive to 95.8 g of the non-aqueous organic solvent.

(Secondary Battery Preparation)

A pouch type lithium secondary battery was prepared in the same manner as in Example 3 except that the above-prepared non-aqueous electrolyte solution was used instead of the non-aqueous electrolyte solution prepared in Example 3.

EXPERIMENTAL EXAMPLES

Experimental Example 1. Initial Discharge Capacity Evaluation

After each of the lithium secondary batteries prepared in Example 1 and Comparative Example 1 was activated at a constant current (CC) of 0.1 C, each secondary battery was charged at a CC of 0.33 C to 4.20 V under a constant current-constant voltage (CC-CV) condition at 25° C., then subjected to 0.05 C current cut-off, and discharged at 0.33 C under a CC condition to 2.5 V.

After the above charging and discharging were set as one cycle and 3 cycles were performed, initial discharge capacity was measured using PNE-0506 charge/discharge equipment (manufacturer: PNE SOLUTION Co., Ltd., 5 V, 6 A), and the results thereof are presented in FIG. 1.

Figure 1:
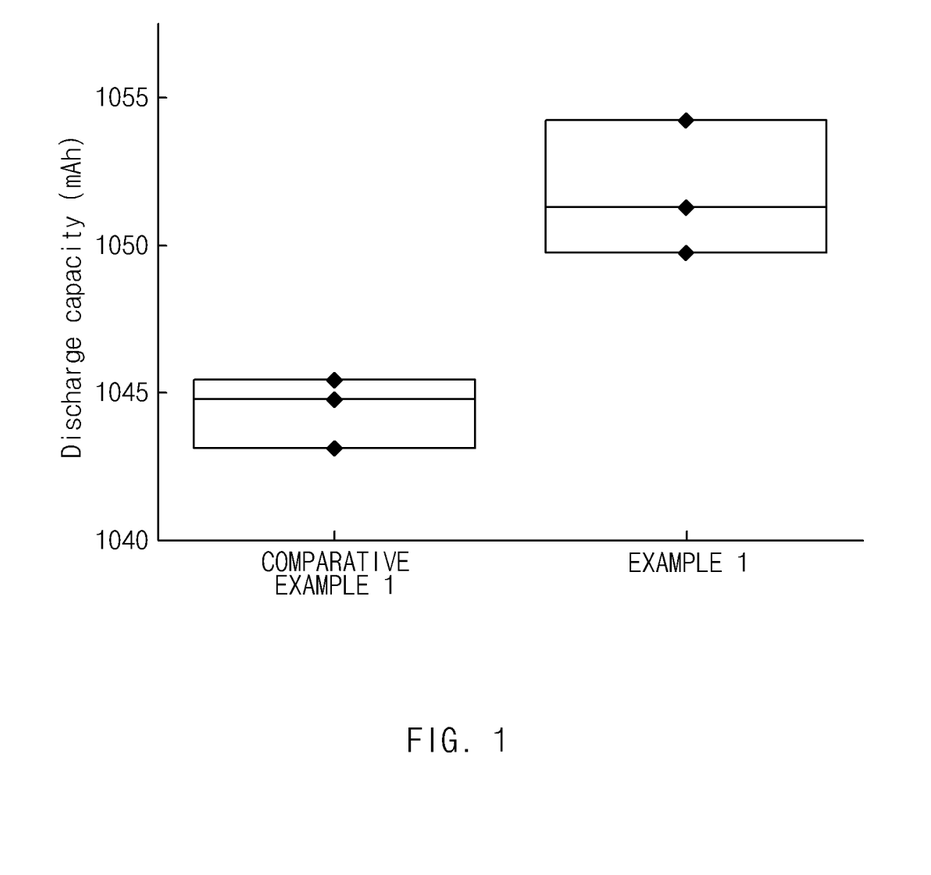
FIG. 1 is a graph illustrating the results of evaluating initial discharge capacities of lithium secondary batteries according to Experimental Example 1 of the present invention.

Referring to FIG. 1, with respect to the secondary battery of Example 1 including the non-aqueous electrolyte solution containing the additive of the present invention, it may be confirmed that initial capacity was higher than that of the secondary battery of Comparative Example 1.

Experimental Example 2. High-Temperature Storage Characteristics Evaluation

After each of the secondary batteries prepared in Example 1 and Comparative Example 1 was activated at a CC of 0.1 C, degassing was performed. Subsequently, each secondary battery was charged at a CC of 0.33 C to 4.20 V under a constant current-constant voltage (CC-CV) condition at 25° C., then subjected to 0.05 C current cut-off, and discharged at a CC of 0.33 C to 2.5 V. The above charging and discharging were set as one cycle, and 3 cycles were performed.

Subsequently, initial discharge capacity was measured using PNE-0506 charge/discharge equipment (manufacturer: PNE SOLUTION Co., Ltd., 5 V, 6 A), a state of charge (SOC) was adjusted to 50%, and a pulse of 2.5 C was then applied for 10 seconds to calculate initial resistance through a difference between a voltage before the pulse application and a voltage after the pulse application.

Next, each secondary battery was recharged at a CC of 0.33 C to a SOC of 100% and then stored at a high temperature of 60° C. for 4 weeks. CC-CV charge and discharge were performed at a CC of 0.33 C after 2 weeks and 4 weeks after the high-temperature storage, and discharge capacities after high-temperature storage were then measured using PNE-0506 charge/discharge equipment (manufacturer: PNE SOLUTION Co., Ltd., 5 V, 6 A).

Figure 2:
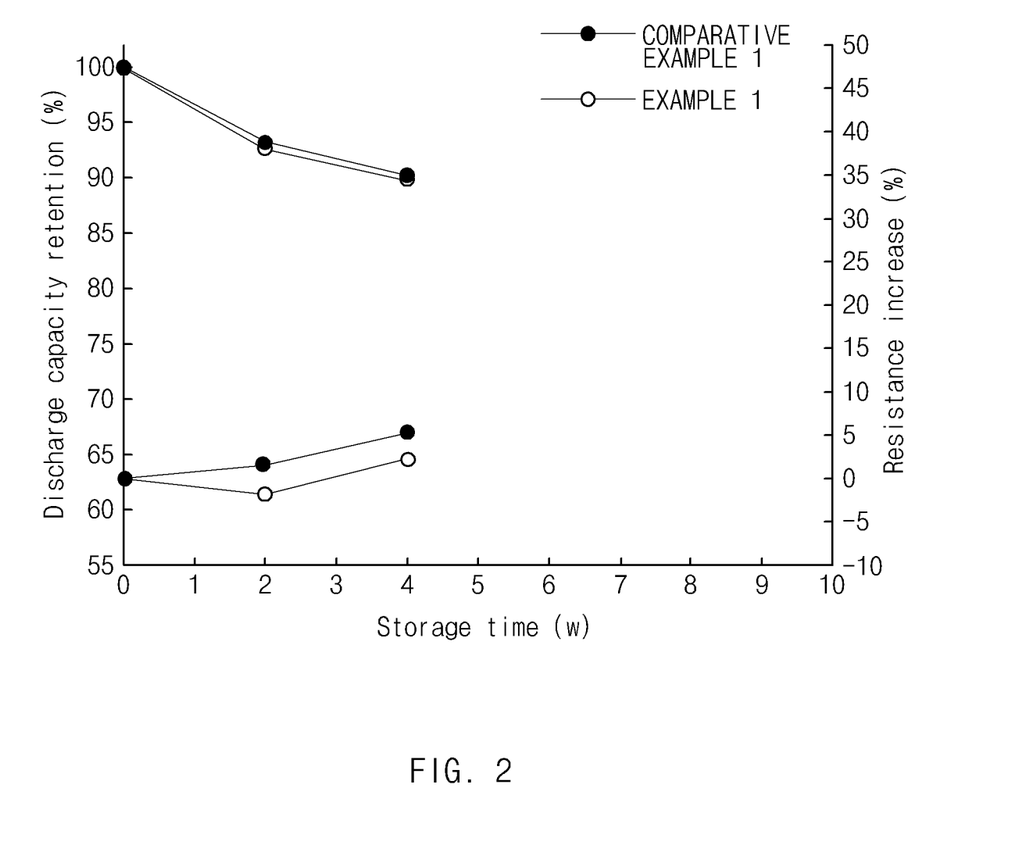
FIG. 2 is a graph illustrating the results of evaluating high-temperature storage characteristics of lithium secondary batteries according to Experimental Example 2 of the present invention.

The measured initial discharge capacity and the discharge capacities after high-temperature storage measured at 2 weeks and 4 weeks were substituted into the following Equation (1) to calculate discharge capacity retention, and the results thereof are presented in FIG. 2.

In this case, after measuring discharge capacities after 2 weeks and 4 weeks, direct current internal resistance (hereinafter, referred to as "DC-iR") was calculated using a voltage drop obtained in a state in which each of the secondary batteries was subjected to a discharge pulse at 2.5 C for 10 seconds at a SOC of 50%, the resistance was substituted into the following Equation (2) to calculate a resistance increase rate (%), and the results thereof are presented in FIG. 2. In this case, the voltage drop was measured using PNE-0506 charge/discharge equipment (manufacturer: PNE SOLUTION Co., Ltd., 5 V, 6 A).

$$\text{Discharge capacity retention (\%)} = \quad \text{Equation (1)}$$
$$(\text{discharge capacity after high-temperature storage/initial discharge capacity}) \times 100$$

$$\text{Resistance increase rate (\%)} = \quad \text{Equation (2)}$$
$$\{(\text{resistance after high-temperature storage} - \text{initial resistance})/\text{initial resistance}\} \times 100$$

Referring to FIG. 2, it may be understood that discharge capacity retentions of the secondary battery of Example 1 and the secondary battery of Comparative Example 1 were similar even after the high-temperature storage for 2 weeks and 4 weeks at a high temperature of 60° C.

However, with respect to the secondary battery of Example 1 including the non-aqueous electrolyte solution containing the additive of the present invention, it may be understood that the resistance increase rate was lower than that of the secondary battery of Comparative Example 1 after 2 weeks of high-temperature storage.

That is, with respect to the lithium secondary battery of the present invention, since the acid ($HF/PF_5$) formed by the pyrolysis of $LiPF_6$ was scavenged by the additive contained in the non-aqueous electrolyte solution and, accordingly, the dissolution of the transition metal from the positive electrode and the degradation of the SEI on the surface of the negative electrode may be suppressed, the degradation of the SEI at high temperature may be further improved in comparison to a conventional electrolyte solution through the modification of SEI components due to reduction and decomposition of the additive, and thus, it may be confirmed that the resistance increase rate during high-temperature storage was significantly improved.

Experimental Example 3. Resistance Increase Rate Evaluation

After each of the lithium secondary battery prepared in Example 1 and the secondary battery prepared in Comparative Example 1 was activated at a CC of 0.1 C, degassing was performed.

Subsequently, each secondary battery was charged at a CC of 0.33 C to 4.20 V under a constant current-constant voltage (CC-CV) condition at 25° C., then subjected to 0.05 C current cut-off, and discharged at a CC of 0.33 C to 2.5 V. The above charging and discharging were set as one cycle, and 3 cycles were performed.

Subsequently, initial discharge capacity was measured using PNE-0506 charge/discharge equipment (manufacturer: PNE SOLUTION Co., Ltd., 5 V, 6 A), a SOC was adjusted to 50%, and a pulse of 2.5 C was then applied for 10 seconds to calculate initial resistance through a difference between a voltage before the pulse application and a voltage after the pulse application.

Next, each secondary battery was charged at a CC of 0.33 C to 4.20 V under a constant current-constant voltage (CC-CV) condition at 45° C., then subjected to 0.05 C current cut-off, and discharged at 0.33 C under a CC condition to 2.5 V. The above charging and discharging were set as one cycle, and 100 cycles of charging and discharging were performed at a high temperature (45° C.)

Subsequently, DC-iR was calculated using a voltage drop obtained in a state in which each of the secondary batteries was subjected to a discharge pulse at 2.5 C for 10 seconds at a SOC of 50%, the resistance was substituted into the following Equation (3) to calculate a resistance increase rate (%), and the results thereof are presented in FIG. 3. In this case, the voltage drop was measured using PNE-0506 charge/discharge equipment (manufacturer: PNE SOLUTION Co., Ltd., 5 V, 6 A).

$$\text{Resistance increase rate (\%)} = \quad \text{Equation (3)}$$
$$\{(\text{resistance after 100 cycles-initial resistance})$$
$$/\text{initial resistance}\} \times 100$$

Figure 3:
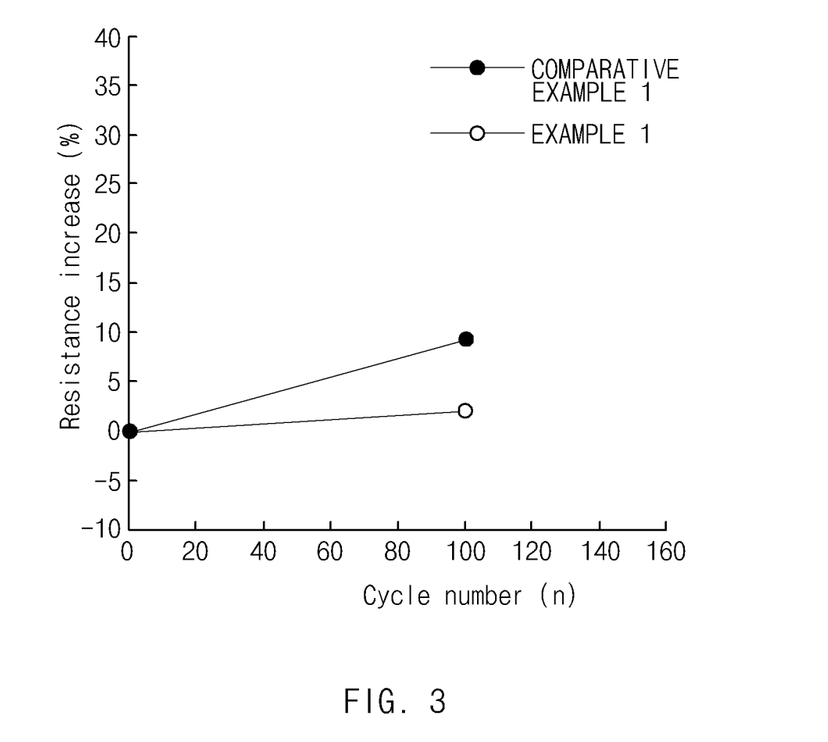
FIG. 3 is a graph illustrating the results of evaluating resistance increase rates of lithium secondary batteries according to Experimental Example 3 of the present invention.

Referring to FIG. 3, with respect to the secondary battery of Example 1 including the non-aqueous electrolyte solution of the present invention, since stable films were formed on the surfaces of the positive/negative electrodes, it may be understood that the resistance increase rate was significantly reduced in comparison to that of the secondary battery of Comparative Example 1 when long-term charge and discharge cycles were performed at high temperature.

Experimental Example 4. Evaluation of formation of SEI

After each of the secondary batteries prepared in Example 1 and Comparative Example 1 was CC-CV charged at 0.1 C to a SOC of 30% to be activated with 0.05 C cut-off, degassing was performed.

Subsequently, discharge capacity was measured using PNE-0506 charge/discharge equipment (manufacturer: PNE SOLUTION Co., Ltd., 5 V, 6 A), and a differential capacity curve, which was obtained by performing the first derivative of a capacity-voltage curve thus obtained, was illustrated in FIG. 4.

Figure 4:
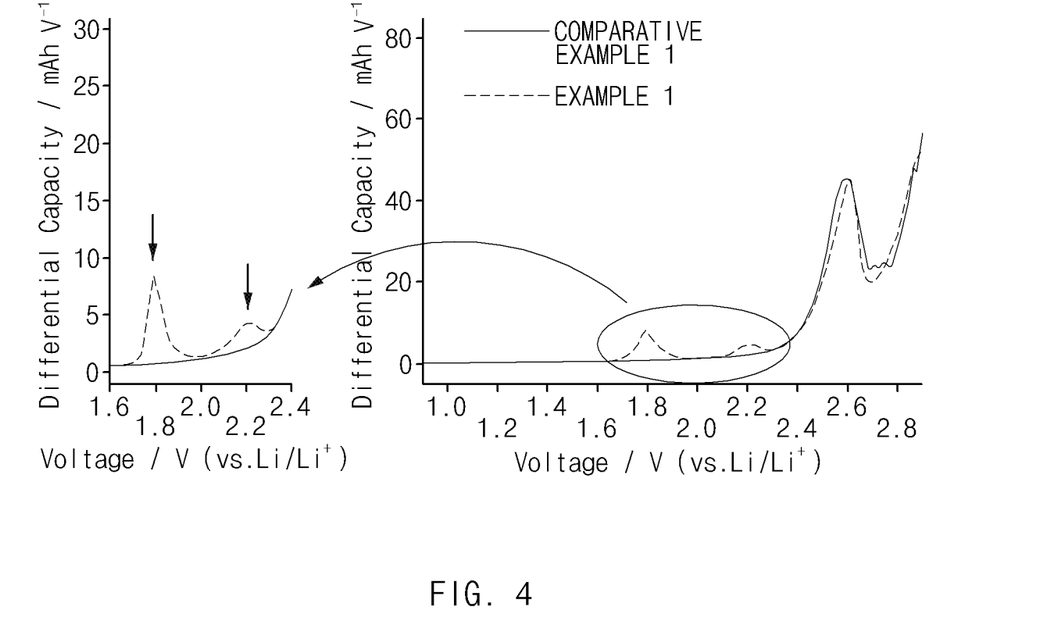
FIG. 4 is a graph illustrating the results of evaluating formation of a solid electrolyte interphase (SEI) of lithium secondary batteries according to Experimental Example 4 of the present invention.

Referring to FIG. 4, with respect to the lithium secondary battery of Example 1 which included the non-aqueous electrolyte solution of the present invention containing the additive, decomposition peaks, showing that the decomposition of the electrolyte solution occurred near voltages of 1.8 V and 2.2 V, were confirmed. According to this behavior, it may be confirmed that another type of SEI was additionally formed on the surface of the negative electrode when the present additive was included.

Experimental Example 5. Metal (Mn) Dissolution Evaluation

A positive electrode active material ($LiMn_2O_4$), carbon black as a conductive agent, and polyvinylidene fluoride (PVDF), as a binder, were added to N-methyl-2-pyrrolidone (NMP), as a solvent, at a weight ratio of 90:7.5:2.5 to prepare a positive electrode mixture slurry (solid content: 50 wt %). A 20 μm thick positive electrode collector (Al foil) was coated with the positive electrode mixture slurry, dried, and then roll-pressed to prepare a positive electrode.

Subsequently, the positive electrode was put in each of the non-aqueous electrolyte solutions (5 mL) prepared in Example 2 and Comparative Example 1 and stored at a SOC of 0% for 2 weeks at 60° C., and a concentration of metal (Mn) dissolved in each electrolyte solution was then measured using an inductively coupled plasma optical emission spectrophotometer (ICP-OES). An amount of the metal measured using ICP analysis is presented in FIG. 5 below.

Figure 5:
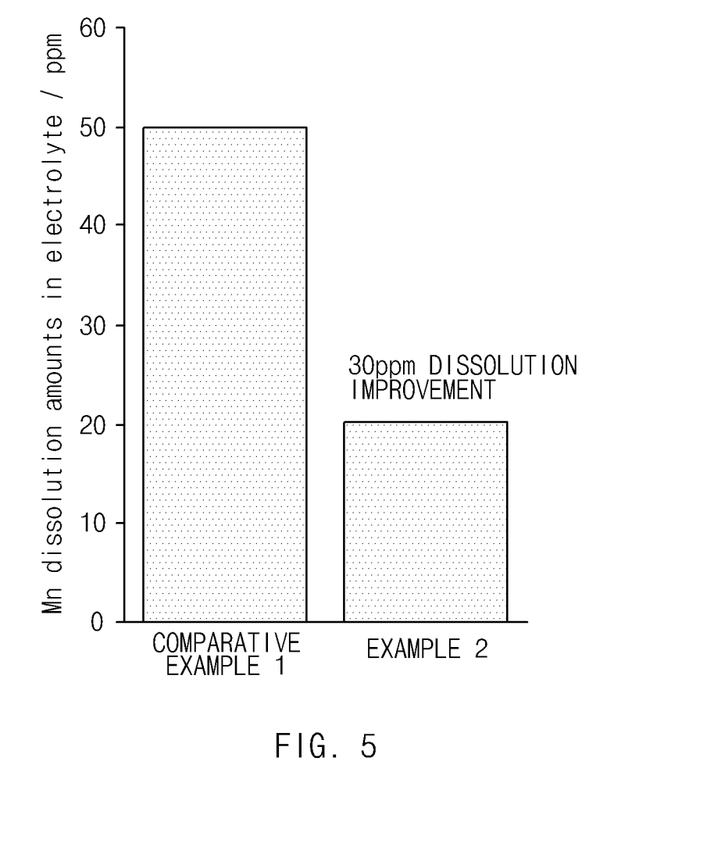
FIG. 5 is a graph illustrating the results of evaluating metal ion dissolution according to Experimental Example 5 of the present invention.

Referring to FIG. 5, in a case in which the non-aqueous electrolyte solution of Example 2 of the present invention was used, since the compound containing a Lewis base, which was included as the additive, may effectively scavenge a Lewis acid as the decomposition product of the anions of the lithium salt which was generated at high temperatures, an effect of suppressing the dissolution of the metal from the positive electrode including the lithium-manganese-based oxide was significantly improved in comparison to the case of using the non-aqueous electrolyte solution of Comparative Example 1 without an additive, and thus, it may be understood that less Mn ions were detected.

Experimental Example 6. High-Temperature Storage Characteristics Evaluation

After each of the secondary batteries prepared in Example 3 and Comparative Example 2 was activated at a CC of 0.1 C, degassing was performed. Subsequently, each secondary battery was charged at a CC of 0.33 C to 4.10 V under a constant current-constant voltage (CC-CV) condition at 25° C., then subjected to 0.05 C current cut-off, and discharged at a CC of 0.33 C to 2.5 V. The above charging and discharging were set as one cycle, and 3 cycles were performed. Subsequently, initial discharge capacity was measured using PNE-0506 charge/discharge equipment (manufacturer: PNE SOLUTION Co., Ltd., 5 V, 6 A), a SOC was adjusted to 50%, and a pulse of 2.5 C was then applied for 10 seconds to calculate initial resistance through a difference between a voltage before the pulse application and a voltage after the pulse application.

Next, each secondary battery was recharged at a CC of 0.33 C to a SOC of 100% and then stored at a high temperature of 45° C. for 20 weeks. CC-CV charge and discharge were performed at a CC of 0.33 C after 20 weeks after the high-temperature storage, and discharge capacity after high-temperature storage was then measured using PNE-0506 charge/discharge equipment (manufacturer: PNE SOLUTION Co., Ltd., 5 V, 6 A).

The measured initial discharge capacity and the discharge capacity after high-temperature storage measured at weeks were substituted into Equation (1) to calculate discharge capacity retention, and the results thereof are presented in Table 1 below.

In this case, after measuring the discharge capacity after 20 weeks, direct current internal resistance (hereinafter, referred to as "DC-iR") was calculated using a voltage drop obtained in a state in which each of the secondary batteries was subjected to a discharge pulse at 2.5 C for 10 seconds at a SOC of 50%, the resistance was substituted into Equation (2) to calculate a resistance increase rate (%), and the results thereof are presented in Table 1 below. In this case, the voltage drop was measured using PNE-0506 charge/discharge equipment (manufacturer: PNE SOLUTION co., Ltd., 5 V, 6 A).

TABLE 1

| | 45° C., 20 weeks storage | |
|---|---|---|
| | Capacity retention (%) | Resistance increase rate (%) |
| Example 3 | 92.6 | −5.03 |
| Comparative Example 2 | 92.2 | −0.93 |

Referring to Table 1, it may be understood that both discharge capacity retention and resistance increase rate of the secondary battery of Example 3 were improved in comparison to those of the secondary battery of Comparative Example 2 even after the high-temperature storage for 20 weeks at a high temperature of 45° C. That is, with respect to the lithium secondary battery of the present invention, since the acid ($HF/PF_5$) formed by the pyrolysis of $LiPF_6$ was scavenged by the additive contained in the non-aqueous electrolyte solution and, accordingly, the dissolution of the transition metal from the positive electrode and the degradation of the SEI on the surface of the negative electrode may be suppressed, the degradation of the SEI at high temperature may be further improved in comparison to the conventional electrolyte solution through the modification of the SEI components due to the reduction and decomposition of the additive, and thus, it may be confirmed that the capacity retention and the resistance increase rate during high-temperature storage were significantly improved.

The invention claimed is:

1. A non-aqueous electrolyte solution for a lithium secondary battery, the non-aqueous electrolyte solution comprising: a lithium salt; an organic solvent; and a compound represented by Formula 1 as a first additive,

[Formula 1]

wherein, in Formula 1,

$R_1$ to $R_4$ are each independently hydrogen or a substituted or unsubstituted alkyl group having 1 to 5 carbon atoms.

2. The non-aqueous electrolyte solution according to claim 1, wherein, in Formula 1, $R_1$ and $R_4$ are each independently a substituted or unsubstituted alkyl group having 1 to 5 carbon atoms, and $R_2$ and $R_3$ are each independently hydrogen or a substituted or unsubstituted alkyl group having 1 to 5 carbon atoms.

3. The non-aqueous electrolyte solution according to claim 1, wherein, in Formula 1, $R_1$ and $R_4$ are each independently a substituted or unsubstituted alkyl group having 1 to 4 carbon atoms, and $R_2$ and $R_3$ are each independently hydrogen or a substituted or unsubstituted alkyl group having 1 to 3 carbon atoms.

4. The non-aqueous electrolyte solution according to claim 1, wherein, in Formula 1, $R_1$ and $R_4$ are each independently a substituted or unsubstituted alkyl group having 1 to 3 carbon atoms, and $R_2$ and $R_3$ are hydrogen.

5. The non-aqueous electrolyte solution according to claim 1, wherein the compound represented by Formula 1 comprises a compound represented by Formula 1a:

[Formula 1a]

6. The non-aqueous electrolyte solution according to claim 1, wherein an amount of the first additive is in a range of 0.01 wt % to 5 wt % based on a total weight of the non-aqueous electrolyte solution.

7. The non-aqueous electrolyte solution according to claim 1, wherein an amount of the first additive is in a range of 0.1 wt % to 3 wt % based on a total weight of the non-aqueous electrolyte solution.

8. The non-aqueous electrolyte solution according to claim 1, further comprising a second additive, wherein the second additive is at least one of vinylene carbonate (VC), 1,3-propane sultone (PS), or ethylene sulfate (Esa).

9. The non-aqueous electrolyte solution according to claim 6, further comprising a third additive, wherein the third additive is for forming a solid electrolyte interphase (SEI), and the third additive is at least one of a halogen-substituted or unsubstituted cyclic carbonate compound, a nitrile compound, a phosphate compound, a borate compound, a lithium salt compound, a sulfate compound, a sultone compound, a fluorinated benzene compound, or a silane compound.

10. A lithium secondary battery comprising the non-aqueous electrolyte solution according to claim 1.

* * * * *